(12) United States Patent
Paget et al.

(10) Patent No.: US 10,106,756 B2
(45) Date of Patent: Oct. 23, 2018

(54) METHOD FOR PRODUCING BIOMETHANE INCORPORATING THE PRODUCTION OF HEAT FOR THE METHANISER USING MEMBRANE SEPARATION

(71) Applicant: L'Air Liquide, Societe Anonyme pour l'Etude et l'Exploitation des Procedes Georges Claude, Paris (FR)

(72) Inventors: Nicolas Paget, Saint Martin d'Heres (FR); Delphine Garnaud, Grenoble (FR); Guénaël Prince, Saint Egreve (FR); Mathieu Lefebvre, Saint Nazaire les Eymes (FR)

(73) Assignee: L'Air Liquide Societe Anonyme Pour L'Etude Et L'Exploitation Des Procedes Georges Claude, Paris (FR)

( * ) Notice: Subject to any disclaimer, the term of this patent is extended or adjusted under 35 U.S.C. 154(b) by 0 days.

(21) Appl. No.: 15/037,198

(22) PCT Filed: Nov. 6, 2014

(86) PCT No.: PCT/FR2014/052829
§ 371 (c)(1),
(2) Date: May 17, 2016

(87) PCT Pub. No.: WO2015/071575
PCT Pub. Date: May 21, 2015

(65) Prior Publication Data
US 2016/0289580 A1 Oct. 6, 2016

(30) Foreign Application Priority Data
Nov. 18, 2013 (FR) ...................... 13 61271

(51) Int. Cl.
| C10L 3/10 | (2006.01) |
| C10L 3/08 | (2006.01) |
| C12P 5/02 | (2006.01) |
| B01D 53/22 | (2006.01) |

(52) U.S. Cl.
CPC .............. *C10L 3/104* (2013.01); *B01D 53/22* (2013.01); *C10L 3/08* (2013.01); *C12P 5/023* (2013.01); *B01D 2258/05* (2013.01); *C10L 2290/02* (2013.01); *C10L 2290/06* (2013.01); *C10L 2290/10* (2013.01); *C10L 2290/26* (2013.01); *C10L 2290/30* (2013.01); *C10L 2290/46* (2013.01); *C10L 2290/548* (2013.01); *Y02E 50/343* (2013.01)

(58) Field of Classification Search
None
See application file for complete search history.

(56) References Cited

U.S. PATENT DOCUMENTS

| 2011/0023497 A1* | 2/2011 | Assmann | .................. C10L 3/08 60/780 |
| 2016/0176768 A1* | 6/2016 | Norddahl | ............... C12M 21/04 71/10 |

FOREIGN PATENT DOCUMENTS

| DE | 20 2008 016134 | 4/2009 |
| DE | 10 2007 058548 | 6/2009 |
| EP | 1 634 946 | 3/2006 |
| JP | 2009 242773 | 10/2009 |

OTHER PUBLICATIONS

International Search Report and Written Opinion for PCT/FR2014/052829, dated Jan. 9, 2015.
French Search Report and Written Opinion for FR 1 361 271, dated Jul. 31, 2014.
Molino, et al., "Biomethane production by anaerobic digestion of organic waste," FUEL, vol. 103, Jan. 1, 2013, pp. 103-109.

* cited by examiner

*Primary Examiner* — Michelle F. Paguio Frishing
(74) *Attorney, Agent, or Firm* — Christopher J. Cronin

(57) ABSTRACT

The present invention relates to a process for producing biomethane suitable for supplying a natural gas network that incorporates a process for providing heat for heating the biogas production step, the process comprising at least steps of producing biogas by anaerobic fermentation of organic matter, of pretreating and compressing the biogas and also of permeation in order to obtain, after a first separation by permeation, a stream of biomethane and a gaseous permeate having a reduced methane content; the process additionally provides the heat necessary for the anaerobic fermentation step via a boiler using the retentate from a second permeation step fed by the permeate from the first separation.

10 Claims, 1 Drawing Sheet

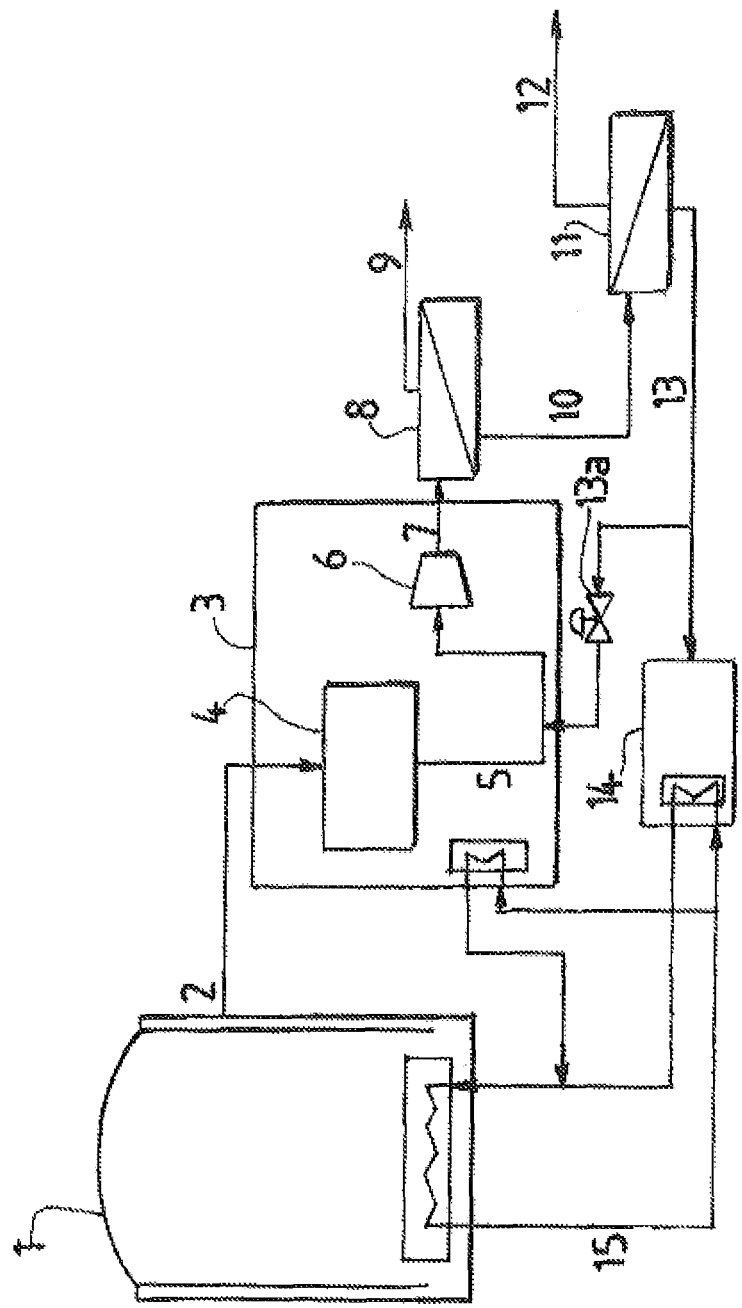

METHOD FOR PRODUCING BIOMETHANE INCORPORATING THE PRODUCTION OF HEAT FOR THE METHANISER USING MEMBRANE SEPARATION

CROSS-REFERENCE TO RELATED APPLICATIONS

This application is a § 371 of International PCT Application PCTFR2014/052829, filed Nov. 6, 2014, which claims § 119(a) foreign priority to French patent application FR1361271, filed Nov. 18, 2013.

BACKGROUND

Field of the Invention

The present invention relates to a process for producing biomethane suitable for supplying a natural gas network that incorporates a process for providing heat for heating the biogas production step; the process comprises at least steps of producing biogas by anaerobic fermentation of organic matter, of pretreating and compressing the biogas and also of permeation in order to obtain, after a first separation, a stream of biomethane and a gaseous permeate having a reduced methane content; at the same time, the process provides the heat necessary for the anaerobic fermentation step.

Related Art

Biomethane is a methane-rich gas obtained via a suitable purification from biogas, and has the same characteristics as natural gas for which it may be substituted.

Added more recently to the upgrading—mainly on-site or nearby—of biogas is that of this biogas purified to the specifications of natural gas. The biomethane produced may thus be used as a non-fossil substitute for natural gas, supplementing natural gas resources with a renewable portion produced at the heart of territories. It can be used for exactly the same purposes.

In particular, within the context of the upgrading thereof, biomethane—a renewable substitute for natural gas that has the same properties as the latter—may be injected into a natural gas distribution or transport network that makes it possible to connect gas producers and consumers.

A natural gas distribution or transport network makes it possible to supply consumers with natural gas. The network is maintained at a pressure between 2 and 6 bar for distribution, 15 and 25 bar for medium-pressure distribution and 25 and 80 bar for transport.

As for biogas, it is a gas produced by the natural or controlled fermentation of plant or animal organic matter (methanization). The characteristic component of biogases is methane, which is formed during the biochemical degradation of organic waste, the other main constituent is carbon dioxide. A biogas also contains, but in smaller proportions, water, nitrogen, hydrogen sulphide, oxygen, and also other organic compounds, in trace amounts.

Depending on the organic matter and the techniques used, the proportions of the components differ, but on average a biogas comprises, as dry gas, from 30% to 75% methane, from 15% to 60% $CO_2$, from 0 to 5% nitrogen, from 0 to 5% oxygen and trace compounds.

Biogas is produced by methanization of organic matter, that is to say by anaerobic fermentation. It is produced in a sealed tank also referred to as a methanizer or digester. It is necessary to operate in the absence of air (anaerobic process) and to maintain a stable temperature in the chamber of the reactor. This temperature depends on the methanization process, that is to say on the type of bacteria used for the degradation of the organic matter, but in all cases it will be necessary to provide heat, thus for a mesophilic process the temperature should be maintained between 30° C. and 37° C., whilst a thermophilic process requires a temperature of from 50° C. to 55° C.

Thus, since the continuous addition of organic matter at a temperature lower than that of the methanizer and also the outside temperature contribute to the cooling of said methanizer, it is necessary to make provision for providing heat for the biogas production step. The heat to be provided may thus represent from 5% to 20% of the energy contained in the biogas produced.

At the same time, in order to be able to benefit from subsidized rates for the purchase of biomethane during the injection to the network, it is necessary for the source that provides the heat for the methanization to use renewable energy.

In order to address this twofold problem, the heat source most commonly used is the biogas produced by the digester. In this case, the heat is provided to the methanization process by heat exchange with boiler water, this being heated using biogas withdrawn before purification to the biogas produced. The portion of biogas thus withdrawn before purification does not therefore participate in the final production.

Yet, in order to be able to upgrade their production in the form of substitute natural gas in a worthwhile manner, biogas producers must be able to have the largest possible production since (i) the purification of biogas is expensive in terms of investment and (ii) it is necessary to be able to provide sufficient amounts of biomethane in order to have outlets—very particularly in the case of small productions.

Being able to use the largest possible portion of biogas to produce biomethane is therefore essential, and even imperative for a small producer whose biogas production may be of the order of twenty $Nm^3/h$ to several tens of $Nm^3/h$. For these small producers, being able to use the largest possible portion of the methane produced, up to 99% of the methane produced or even more, may be a major advantage.

At the same time, in order to benefit from subsidized rates for the purchase of biomethane during the injection to the network, it remains imperative to utilize a heat source that uses renewable energy.

Solutions exist that propose to recover available heat produced by the purification unit (heat of the compressor or of the cold units) but the supply of heat from this source is not sufficient for the total requirements of the digester (it only covers around 20% of the requirements).

Another known solution consists in recovering the heat produced by a system for destroying vented gases via a low-GCV boiler burning a biogas containing between 10% and 20% methane, preferably 15% methane, or by thermal oxidation which is applicable for gases containing between 2% and 8% methane, preferably 5% methane. However, these solutions for destroying vented gases are expensive, too expensive for small projects. Moreover, they only make it possible to provide the methanizer with a small portion of the heat needed (the solution covers at most 15% of the requirements).

Therefore, no solution exists to date that makes it possible to provide the methanizer with all of the heat needed which simultaneously:

is derived from the biomethane production process and therefore uses renewable energy, keeps all of the biogas production available for purification, does not involve large additional costs, which would be excessive for a small producer and therefore does not require expensive supplementary treatments in order to provide the means for heating the methanizer.

SUMMARY OF THE INVENTION

One objective of the invention is to overcome these deficiencies and to provide biomethane producers with a solution that enables them to heat the feedstock present in the methanizer which meets the stated requirements.

According to the invention, a process is thus proposed for producing biomethane intended for supplying a natural gas network and that incorporates a process for providing heat for heating the biogas production step, wherein:

the biomethane production process comprises at least:
a step (a) of producing biogas by methanization of organic matter,
a step (b) of pretreating all of the biogas produced during step (a),
a step (c) of compressing all of the pretreated biogas,
a step (d) of separating by permeation all of the pretreated and compressed biogas resulting from step (c) in order to produce a gaseous retentate having a methane content of greater than 89%, preferably greater than 96.5% and a gaseous permeate having a methane content of between 10% and 25%, preferably of the order of 20%,
a step (e) of providing the gaseous retentate from step (d) as biomethane,
the process for heating the biogas production step (a) comprises at least:
a step (f) of providing heat to step (a) via a heating water circuit,
a step (g) of heating said heating water in a gas boiler,
characterized in that said process for providing heat also comprises at least:
a step (h) of separating by permeation the gaseous permeate resulting from the first permeation separation step (d) in order to produce a methane-enriched gaseous retentate, the methane content of which is greater than or equal to 25%, preferably between 30% and 40%, more preferably of the order of 35% and a methane-depleted permeate,
a step (i) of supplying the burners of the boiler from step (g) with the retentate from the separation step (h),
a step (j) of discharging the permeate produced by the permeation separation step (h).

The process according to the invention thus proposes to integrate the purification of the biogas to biomethane and the production of heat for the digester. All of the biogas is sent to the purifier without diverting a portion of the production in order to produce heat; this may constitute a significant difference, especially for small producers since when the production is too small it cannot find an outlet to a network.

Membrane purification technology enables an effective separation of the $CO_2$ and of the $CH_4$. It is therefore possible to obtain a biomethane having the quality required by the network operator by means of a single membrane stage. Indeed, at the outlet of this first membrane stage, an enriched gas is produced, the methane concentration of which is greater than 89%, possibly being, depending on the quality required by the client, greater than 96.5%.

The concentration of $CH_4$ in the permeate of this first membrane is between 10% and 25%, preferably of the order of 20%, and does not enable the use of gas boilers of simple technology; specifically, these require a methane content of greater than 25%, preferably greater than or equal to 30%.

In order to achieve this minimum content, the process of the invention makes provision to add the permeate to a second membrane stage. This solution represents, for the biogas producer, an initial investment and an operating cost that are 30% to 50% lower relative to a conventional purification system and a conventional heating system. The retentate produced by this second membrane stage is a gas enriched in $CH_4$ to a methane content of greater than 25%, preferably between 30% and 40% which may be used in a simple gas boiler. The permeate from this second stage is very depleted in $CH_4$, it may be discharged to the atmosphere without expensive treatment of the vented gases. Less than 2%, preferably less than 1% of the $CH_4$ produced by the methanizer is thus discharged to the atmosphere.

Depending on the case, the process of the invention may comprise all or some of the characteristics below.

The process for heating step (a) comprises a step (k) of additional provision of heat to the water circulating in said heating water circuit using heat recovered during steps (b) and (c). Specifically, heat is in any case available at equipment such as a compressor and cold units; it can be used without excessive investment, thus contributing to the total provision of heat to the methanizer.

A variable fraction of the methane-enriched retentate from the separation step (h) may be sent back to the inlet of the compression step (c) when the supply of heat is greater than the requirements of the biogas production step (a). Specifically, as soon as the heat requirements of the methanizer are met, the extra methane available in the retentate of the second membrane stage is thus recovered in order to be recycled upstream of the membrane separation so as to increase the production of biomethane. For this purpose, a recirculation line equipped with a variable flow valve is thus connected to the line transporting the retentate to the burners of the boiler.

According to a second aspect of the invention, the latter relates to a plant suitable for carrying out the process of the invention.

In particular, it relates to a plant for producing biomethane intended for supplying a natural gas network and the integrated provision of heat for heating the biogas production step comprising at least:

a biomethane production unit comprising at least:
a source of organic matter,
a methanizer for producing biogas by methanization of said organic matter,
a module for pretreating the biogas produced,
a compressor suitable for compressing the prepurified biogas,
a first module for separating, by membrane permeation, the pretreated and compressed biogas suitable for producing a gaseous retentate having a methane content of greater than 89%, preferably greater than 96.5% and a gaseous permeate having a methane content of between 10% and 25%, preferably of the order of 20%,
a means for providing the gaseous retentate resulting from said first separation module as biomethane produced,
means suitable for cooperating in order to heat the organic matter contained in the methanizer comprising at least:
a heating water circuit suitable for heating the methanizer,
a gas boiler suitable for heating the water of said heating water circuit,
characterized in that the means suitable for cooperating in order to heat said organic matter comprise:

a second module for separating, by membrane permeation, the gaseous permeate resulting from the first permeation separation module suitable for producing a methane-enriched gaseous retentate, the methane content of which is greater than 25%, preferably between 30% and 40%, more preferably of the order of 35% and a methane-depleted permeate, a means for supplying the burners of said gas boiler with the retentate from the second separation module, a means for discharging the permeate resulting from the second separation module.

According to one advantageous embodiment of the invention, the means suitable for cooperating in order to heat the organic matter contained in the digester comprise additional means suitable for recovering heat from the biogas pretreatment module and the pretreated biogas compressor and also additional means suitable for providing the heat recovered to the water of the heating circuit of the digester.

Advantageously, the plant additionally comprises means suitable for recycling a fraction of the retentate from the second membrane stage to the inlet of the pretreated biogas compressor, said means comprising a line equipped with a flow control valve that, as a function of the heat requirement, makes it possible to recirculate the excess gas going toward the boiler to upstream of the compressor. The objective is to provide the digester with only the heat needed.

The invention will now be better understood owing to the following description given with reference to the sole appended FIGURE.

BRIEF DESCRIPTION OF THE FIGURES

The FIGURE presents a schematic diagram illustrating various elements of the invention. For the sake of simplicity, only the elements of the plant useful for the understanding and implementation of the invention are referenced.

DETAILED DESCRIPTION OF THE INVENTION

According to the diagram of the FIGURE, the biomethane production plant according to the invention operates in the following manner. The methanizer 1 delivers a biogas 2. The biogas 2 is sent to a pretreatment module 3 in which it is objected to 4 different treatments prior to a $CO_2/CH_4$ separation. The pretreated biogas 5 is compressed in the compressor 6 in order to provide the compressed pretreated biogas 7 at the inlet pressure to a first membrane stage 8 that carries out the $CO_2/CH_4$ separation. More specifically, the membrane stage 8 delivers a methane-enriched gaseous retentate 9, the methane content of which is sufficient to be substituted for natural gas—at least 89%, if necessary 96.5% or more, depending on the specifications of the natural gas that must be substituted—and delivers a gaseous permeate 10 having a methane content of between 10% and 25%. In order to be able to use the methane contained in the permeate 10 as fuel in a simple boiler, the permeate 10 must firstly be enriched in methane, it is thus sent to the feed of a second membrane stage 11 which delivers a methane-depleted permeate 12 (less than 2% of the methane contained in the biogas produced is thus discharged into the permeate) and a retentate 13, the methane content of which is greater than 30%, preferably of the order of 35%. The gaseous stream 13—the methane content of which is thus high enough—is sent to the burners of a boiler 14, which can therefore be a boiler of conventional technology. The permeate 12 is methane-depleted relative to the stream 11, its $CH_4$ content is low enough to be able to be discharged to the atmosphere without expensive additional treatment of the vented gas. The boiler 14 provides heat to the water circuit 15 which heats the organic matter contained in the methanizer 1 in order to maintain therein the required temperature conditions for the correct operation of the anaerobic fermentation process that generates the biogas 2. Additional heat is provided to heat the water circulating in the heating circuit 15 using heat available from the pretreatment module 4 by recovery of heat from cold units and/or heat of compression from the compression module 7.

When the heat requirements of the fermentation are lower than the available resources, a portion 13a of the stream 13 is drawn off from the stream supplying the boiler and is sent to the compressor 6 in order to be purified in addition to the stream of biogas 5. This flow 13a is controlled owing to a regulated FCV1 (flow control valve 1) valve installed on the line ensuring the recycling thereof to the compressor so as to adapt the flow as a function of the heat requirements of the methanizer. The table below presents the characteristics of the various streams resulting from the implementation of the invention applied to a pretreated biogas stream 5 containing 55% methane and 44.4% carbon dioxide. The percentages expressed are molar percentages, the contents of minor elements are not indicated—namely for example 0.6% for the biogas 5.

| | Stream ref. | | | | | |
|---|---|---|---|---|---|---|
| Charact | 5 | 7 | 9 | 10 | 12 | 13 |
| % $CH_4$ | 55 | 55 | 96.91 | 21.01 | 03.80 | 34.25 |
| % $CO_2$ | 44.4 | 44.4 | 02.29 | 78.24 | 95.54 | 64.92 |
| P. bar | 1.05 | 15.25 | 15 | 2.6 | 1.015 | 1.9 |
| $Nm^3/h$ | 51.32 | 51.05 | 22.54 | 28.52 | 12.40 | 16.12 |
| Function: | Biogas | Memb.1 feed | $BioCH_4$ | Memb.2 feed | Vented gas | Fuel |

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", an and the include plural referents, unless the context clearly dictates otherwise.

"Comprising" in a claim is an open transitional term which means the subsequently identified claim elements are a nonexclusive listing i.e. anything else may be additionally included and remain within the scope of "comprising," "Comprising" is defined herein as necessarily encompassing the more limited transitional terms "consisting essentially of" and "consisting of", "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A process for producing biomethane suitable for supplying a natural gas network that incorporates a process for providing heat for heating the biogas production step, wherein the biomethane production process comprises at least:
    a step (a) of producing biogas by methanization of organic matter;
    a step (b) of pretreating the biogas produced during step (a);
    a step (c) of compressing the pretreated biogas with a compressor;
    a step (d) of using a first gas separation module to separate, by permeation, the pretreated and compressed biogas resulting from step (c) in order to produce, in comparison to the pretreated and compressed biogas, a first methane-enriched gaseous retentate having a methane content of greater than 89% and a first methane-depleted gaseous permeate having a methane content of between 10% and 25%;
    a step (e) of providing the gaseous retentate from step (d) as biomethane;
    a step (f) of heating water in a heating water circuit including a gas boiler having burners, heat being provided to step (a) via the heating water circuit;
    a step (g) of separating by permeation the first methane-depleted gaseous permeate to produce, in comparison to the first methane-depleted gaseous permeate, a second methane-enriched gaseous retentate and a second methane-depleted permeate, the methane content of the second methane-enriched gaseous retentate of step (g) being greater than or equal to 25%;
    a step (h) of supplying the burners of the boiler from step (f) with the second methane-enriched gaseous retentate from the separation step (g) as fuel for consumption by the burners; and
    a step (i) of discharging the permeate produced by the permeation separation step (g).

2. The process of claim 1, further comprising a step (j) of providing additional heat to the water circulating in said heating water circuit using heat recovered during steps (b) and (c).

3. The process of claim 1, wherein a variable fraction of the methane-enriched retentate from the separation step (g) is sent back to an inlet of the compressor of step (c) when the supply of heat to step (a) is greater than heat requirements of step (a).

4. The process of claim 1, wherein the gaseous retentate resulting from performance of step (d) has a methane content of greater than 96.5%.

5. The process of claim 1, wherein the gaseous retentate resulting from performance of step (g) has a methane content of between 30% and 40%.

6. A plant for carrying out the process of claim 1 for producing biomethane intended for supplying a natural gas network and the integrated provision of heat for heating the biogas production step, said plant comprising at least:
    a biomethane production unit comprising at least a source of organic matter, a digester for producing biogas by methanization of said organic matter, and a module for prepurifying the biogas produced;
    a compressor suitable for compressing the prepurified biogas;
    a first gas separation module for separating, by membrane permeation, the prepurified and compressed biogas, said first module being suitable for producing a gaseous retentate having a methane content of greater than 89% and a gaseous permeate having a methane content of between 10% and 25%;
    a system for heating the organic matter contained in the digester comprising at a heating water circuit suitable for heating the digester and a gas boiler being suitable for heating the water of the heating water circuit; and
    a second module for separating, by membrane permeation, the gaseous permeate resulting from the first permeation separation module, said second module being suitable for producing a methane-depleted permeate and a methane-enriched gaseous retentate having methane content greater than 25, wherein the second module provides the gaseous retentate retentate thereof as biogas, the second separation module supplies the retentate thereof to the burners of said gas boiler, and the second separation module discharges the permeate resulting therefrom.

7. The plant of claim 6, wherein the means suitable for cooperating in order to heat the organic matter contained in the digester comprise additional means suitable for recovering heat from the biogas prepurification module and the prepurified biogas compressor and also additional means suitable for providing the heat recovered to the water of the heating circuit of the digester.

8. The plant of claim 6, further comprising a line equipped with a flow control valve suitable for recycling a fraction of the retentate from the second membrane stage to the inlet of the compressor.

9. The plant of claim 6, wherein said first module is suitable for producing a gaseous retentate having a methane content of greater than 96.5%.

10. The plant of claim 6, wherein a second module is suitable for producing the methane-enriched gaseous retentate at a methane content of between 30% and 40%.

* * * * *